US00PP36974P2

(12) United States Plant Patent
Bennett

(10) Patent No.: US PP36,974 P2
(45) Date of Patent: Sep. 23, 2025

(54) SHRUB ROSE PLANT NAMED 'AUSCP17960'

(50) Latin Name: *Rosa hybrida*
Varietal Denomination: AUSCP17960

(71) Applicant: DAVID AUSTIN ROSES LIMITED, Wolverhampton (GB)

(72) Inventor: Carl Bennett, Wolverhampton (GB)

(73) Assignee: DAVID AUSTIN ROSES LIMITED, Albrighton (GB)

( * ) Notice: Subject to any disclaimer, the term of this patent is extended or adjusted under 35 U.S.C. 154(b) by 0 days.

(21) Appl. No.: 19/083,777

(22) Filed: Mar. 19, 2025

(30) Foreign Application Priority Data

Jan. 20, 2025 (QZ) ..... PBR 20250140

(51) Int. Cl.
*A01H 5/02* (2018.01)
*A01H 6/74* (2018.01)

(52) U.S. Cl.
USPC ..... Plt./107

(58) Field of Classification Search
USPC ..... Plt./101, 102, 107
See application file for complete search history.

(56) References Cited

U.S. PATENT DOCUMENTS

PP32,662 P2 * 12/2020 Austin ..... A01H 5/02
Plt./372

* cited by examiner

*Primary Examiner* — Susan McCormick Ewoldt
(74) *Attorney, Agent, or Firm* — Panitch Schwarze Belisario & Nadel LLP; Stephany G. Small; Travis W. Bliss

(57) ABSTRACT

A new and distinct variety of shrub rose plant, referred to by its cultivar name, 'AUSCP17960', is described. The new variety forms in abundance on a substantially continuous basis, double, pink-colored blossoms. The growth habit is upright. Dark green ornamental foliage is formed. Additionally, the new variety is particularly well suited for growing as distinctive ornamentation in the landscape.

1 Drawing Sheet

Latin name of genus and species of plant claimed: *Rosa hybrida.*

Variety Denomination: 'AUSCP17960'.

CROSS REFERENCE TO RELATED APPLICATIONS

This application claims priority to Plant Breeders' Right Application No. 2025/0140, which was filed at Community Plant Variety Office in the European Union on Jan. 20, 2025, the contents of which are hereby incorporated by reference for all purposes.

BACKGROUND OF THE INVENTION

The new variety of shrub rose plant of the present invention was created by controlled breeding during June 2013, in Wolverhampton, United Kingdom by artificial pollination wherein two parents were crossed which previously had been studied in the hope that they would contribute the desired characteristics. The female parent (i.e., the seed parent) of the new variety was an unnamed seedling (not patented). The male parent (i.e., the pollen parent) of the new variety was a different unnamed seedling (not patented).

The parentage of the new variety can be summarized as follows:

unnamed seedling x different unnamed seedling

The seeds resulting from the above pollination were sown and small plants were obtained which were physically and biologically different from each other. Selective study resulted in the identification of a single plant of the new variety.

The new variety has been found to undergo asexual propagation in Albrighton, United Kingdom by a number of routes such as stem cuttings. Asexual propagation techniques in Albrighton, United Kingdom, such as stem cuttings, have shown that the characteristics of the new variety are homogeneous, stable, and strictly transmissible by such asexual propagation from one generation to another. Accordingly, the new variety undergoes asexual propagation in a true-to-type manner.

SUMMARY OF THE INVENTION

It was found that the new variety of shrub rose plant of the present invention possesses the following combination of characteristics:

(a) forming double, pink-colored blossoms,
(b) exhibiting an upright growth habit, and
(c) providing ornamental dark green foliage.

The new variety well meets the needs of the horticultural industry. It can be grown to advantage as ornamentation in parks, gardens, public areas, and residential landscapes. Accordingly, it is particularly well suited for growing in the landscape.

The new variety can be readily distinguished from its ancestors. More specifically, the new variety displays a lower petal count and longer vase life when cut from the plant compared to the seed parent. Additionally, the new variety displays pink-colored blooms and a longer vase life when cut from the plant compared to the yellow-colored blooms and poor vase life of the pollen parent. Moreover, the new variety can be readily distinguished from non-parental related similar varieties. For example, the new variety displays a higher petal count, forms a rounded flower shape, displays a larger basal spot on the petal, and exhibits a weaker leaflet margin undulation compared to the 'AUSIMAGE' variety (U.S. Plant Pat. No. 32,662) which displays fewer petals, forms an irregularly rounded flower shape, displays a smaller basal spot on the petal, and exhibits a medium-strong leaflet margin undulation.

The new variety has been named the 'AUSCP17960' variety.

BRIEF DESCRIPTION OF THE PHOTOGRAPHS

The accompanying photograph shows, as nearly true as it is reasonably possible to make the same in a color illustration of this character, a typical specimen of the new variety and blossoms of the new variety. The illustrated rose plant of the new variety was approximately three years of age and was grown in a greenhouse on its own roots in Albrighton, United Kingdom. The photograph was taken May 2024.

Drawing—illustrates individual plant parts of the new variety.

DETAILED BOTANICAL DESCRIPTION

The chart used in the identification of colors is that of The Royal Horticultural Society (The R.H.S. Colour Chart, 2001 edition). The terminology which precedes reference to the chart has been added to indicate the corresponding color in more common terms and The R.H.S. Colour Chart designation used herein represents the closest color observed on the majority of the specified botanical feature. The description is based on a three-years-old specimen of the new variety, observed during May 2024 growing in a greenhouse on its own roots in Albrighton, United Kingdom.

Botanical classification: *Rosa hybrida* cultivar 'AUSCP17960'.

Commercial classification: Shrub Rose.

Plant:

*Habit*.—Upright.

*Height*.—Typically 120 cm to 130 cm.

*Width*.—Approximately 70.0 cm on average.

Branches:

*Stem color*.—Old wood: Yellow-Green Group 144A. — young stems: Yellow-Green Group 144B.

*Length*.—Main stems: approximately 100.0 cm on average. — secondary stems: absent.

*Diameter*.—Main stems: approximately 0.9 cm on average. — secondary stems: absent.

*Texture*.—Smooth.

*Prickles*.—Amount: few. — young prickles: length is approximately 0.4 cm on average; width is approximately 0.2 cm on average at point of attachment; and color is Red Group 46A with some green. — old prickles: length is approximately 0.7 cm on average; width is approximately 0.3 cm on average at point of attachment; and color is Greyed-Orange Group 165D.

*Anthocyanin coloration of young shoots*.—Absent to very weak.

*Internode numbers on entire branch*.—Not recorded.

*Internode length*.—Approximately 6.2 cm on average.

Leaflets:

*Number*.—5 and 7.

*Shape*.—Pointed oval; apex is acuminate; and base is mostly rounded or cordate.

*Arrangement*.—Odd-pinnate.

*Margin*.—Serrate.

*Undulation*.—Weak-medium.

*Glossiness of upper side*.—Weak-medium.

*Texture*.—Upper surface: leathery. — under surface: leathery.

*Venation pattern*.—Reticulate.

*Venation color*.—Upper surface color: Yellow-Green Group 147A. — under surface color. Yellow-Green Group 147A.

*Size*.—Terminal leaflet: length is approximately 7.5 cm on average; width is approximately 5.5 cm on average. — lower leaflets: length is approximately 7.0 cm on average; width is approximately 4.8 cm on average. — leaf: length is approximately 17.6.cm on average; width is approximately 13.0 cm on average.

Foliage:

*Young foliage*.—Upper surface color: Yellow-Green Group 146B with a perimeter of Red Group 53A. — under surface color: Greyed-Purple Group 185B with Yellow-Green Group 144C in the center.

*Old foliage*.—Upper surface color: Yellow-Green Group 147A. — under surface color: Greyed-Green Group 194A.

*Petiole*.—Texture: upper surface is rough; under surface is smooth with prickles and slightly glandular. — length: approximately 5.1 cm on average. — width: approximately 0.18 cm on average. — upper surface color: Green Group 143B. — under surface color: Green Group 143B.

*Rachis*.—Length: not recorded. — width: not recorded. — upper surface color: Green Group 143B. — under surface color: Green Group 143B.

*Stipules*.—Length: approximately 2.3 cm on average. — margin: glandular. — upper surface color: Yellow-Green Group 146A. — lower surface color: Yellow-Green Group 146A.

Inflorescence:

*Number of blossoms per stem or in a cluster*.—Typically 1 bloom per stem on average; other blooms nipped out for single bloom cut rose production.

*Peduncle*.—Color: Yellow-Green Group 144C. — diameter: approximately 0.3 cm on average. — length: approximately 7.0 cm on average. — surface texture: smooth with prickles.

*Sepals*.—Number: 2 lightly appendaged sepals; 3 unappendaged sepals. — upper surface color and texture: Green Group 139C, smooth and hairy. — under surface color and texture: Green Group 143B, smooth. — size: length is approximately 3.2 cm on average; width is approximately 0.9 cm on average. — margin: smooth and slightly hairy. — extensions: absent/very weak. — shape: lanceolate. — apex: acuminate. — base: not recorded.

*Buds*.—Shape: short, blunt topped. — size: length is approximately 2.6 cm on average; width is approximately 1.8 cm on average. — color (when opening): upper surface is Orange-Red Group 30A; under surface is Orange Group 28D.

*Flower*.—Form: double. — profile: upper part is flat; lower part is flat. — shape when viewed from the top: round. — diameter: approximately 10.9 cm on average. — height: approximately 3.5 cm on average. duration: on the plant typically 5 to 7 days; approximately 7 days on average as a cut flower. — petal color when opening: upper surface is Orange-Red Group 31B; lower surface is Red-Purple Group 68D; basal spot is medium and Yellow Group 3B. — petal color when fully open: upper surface is Red-Purple Group 68D with some Red Group 39C at the center; lower surface is Purple Group 75D; basal spot is medium and Yellow Group 3B. — petal color at end of bloom: upper surface fades to Red-Purple Group 68D; lower surface fades to Purple Group 75D. — petals reflex one by one: no.

*Fragrance*.—Moderate, fruity and floral scent.

*Petal*.—Number: approximately 105 on average. — drop: petals hang on and dry. — length: approximately 4.6 cm on average. — width: approximately 4.2 cm on average. — overall shape: oval, obovate. — margin: notched with weak-medium undulation. — apex shape: rounded. — base shape: acute. — texture: smooth, satiny, and thin.

*Petaloids*.—Number: typically 25 to 26. — length: approximately 2.6 cm on average. — width: approximately 1.6 cm on average. — color: upper and under surfaces are Red-Purple Group 65C. — texture: smooth, satiny, and thin. — margin: irregular. — shape: obovate.

*Stamen*.—Number: approximately 10. — anthers: color is Yellow-Orange Group 15C; length is approximately 0.1 cm on average; and shape is standard. — filaments: length is approximately 0.5 cm on average; width is approximately 0.1 cm on average; and color is Yellow-Orange Group 17C.

*Pistils*.—Number: approximately 90. — style: length is approximately 0.8 cm on average; width is approximately 0.1 cm on average; and color is Green-White Group 157A. — stigma: length is approximately 0.1 cm on average; diameter is less than 0.1 cm; shape was not recorded; color is Yellow Group 8A.

*Receptacle*.—Diameter: approximately 1.0 cm on average. — depth: approximately 1.04 cm on average. — shape: pitcher shaped. — color: Green Group 143B. — surface texture: smooth.

*Pollen*.—Amount: scarce. — color: Yellow Group 3C.

*Hips/seed*.—None observed.

Development:

*Blossoming*.—Repeat flowering in Albrighton, United Kingdom; blooms may continue year-round if grown inside a warm greenhouse.

*Resistance to diseases*.—Resistance for powdery mildew (*Podosphaera pannosa*), black spot (*Diplocarpon rosae*) and rust (*Phragmidium tuberculatum*) under normal greenhouse growing conditions in Albrighton, United Kingdom.

*Hardiness*.—Not tested.

The new 'AUSCP17960' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of shrub rose plant named 'AUSCP17960' characterized by the following combination of characteristics:

(a) forming double, pink-colored blossoms, (b) exhibiting an upright growth habit, and (c) providing ornamental dark green foliage;

substantially as herein shown and described.

* * * * *

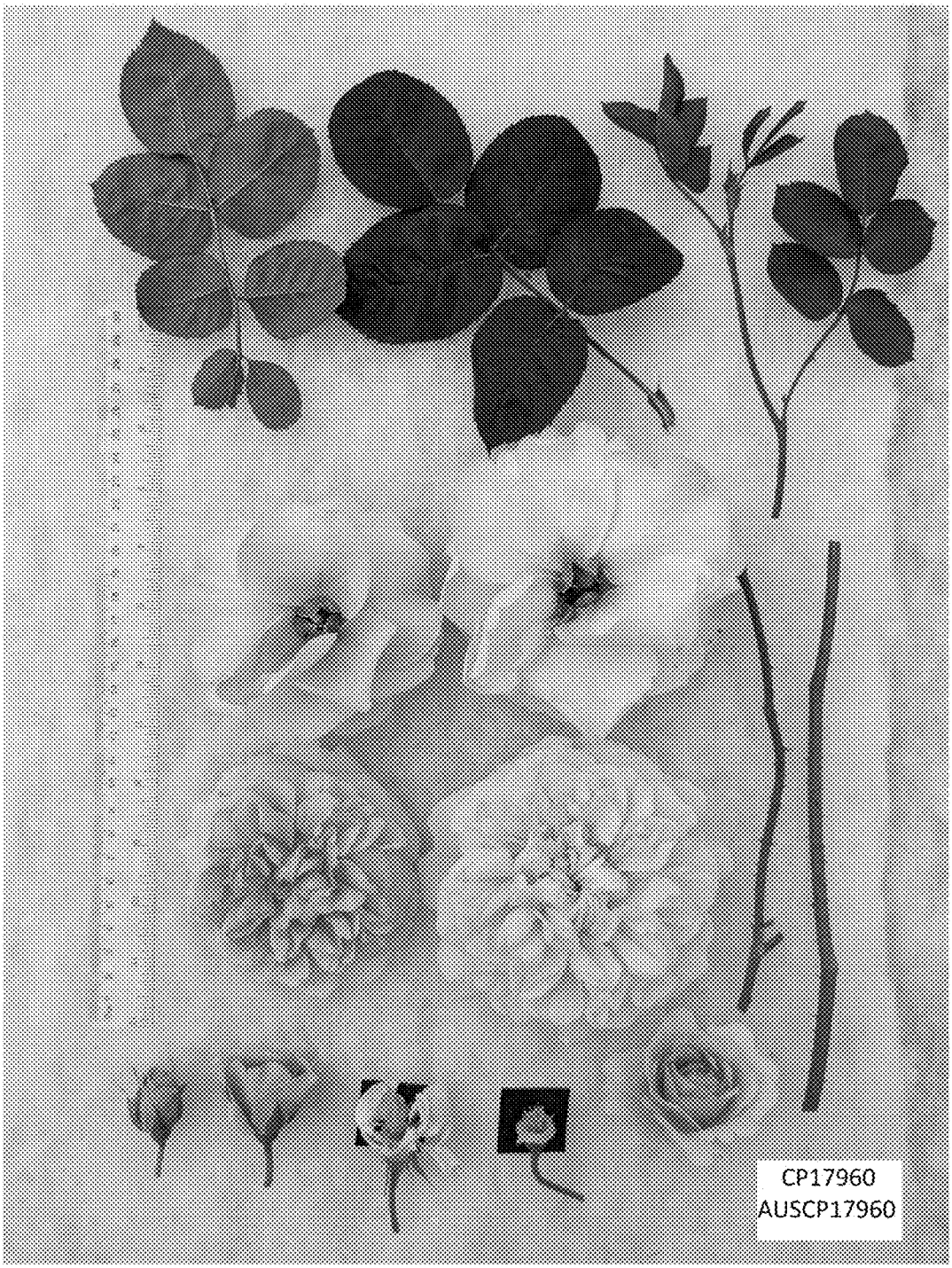
CP17960
AUSCP17960